United States Patent [19]

Scarlett et al.

[11] Patent Number: 5,395,991
[45] Date of Patent: Mar. 7, 1995

[54] PROCESS FOR THE PRODUCTION OF ALCOHOLS AND DIOLS

[75] Inventors: John Scarlett, Spennymoor; Michael W. M. Tuck, London; Michael A. Wood, Middlesbrough, all of England

[73] Assignee: Eastman Chemical Company, Kingsport, Tenn.

[21] Appl. No.: 175,545

[22] Filed: Dec. 30, 1993

[30] Foreign Application Priority Data

Dec. 2, 1993 [GB] United Kingdom ............... 9324786

[51] Int. Cl.$^6$ ............... C07C 29/147; C07C 29/143; C07C 27/04
[52] U.S. Cl. ............................. 568/864; 568/822; 568/830; 568/831; 568/861; 568/862; 568/880
[58] Field of Search ............... 568/822, 830, 864, 831, 568/861, 862, 880

[56] References Cited

U.S. PATENT DOCUMENTS

| | | | |
|---|---|---|---|
| 2,040,944 | 5/1936 | Lazier | 568/844 |
| 2,079,414 | 5/1937 | Lazier | 568/830 |
| 2,091,800 | 8/1937 | Adkins et al. | 568/864 |
| 2,105,664 | 1/1938 | Lazier | 568/864 |

(List continued on next page.)

FOREIGN PATENT DOCUMENTS 143634  6/1985  European Pat. Off. .

(List continued on next page.)

OTHER PUBLICATIONS

Mansour et al., "Sel. Hydrog. of Esters to Alcoh. with a Catal. Obtained Rh$_2$O$_3$, Sn (n-C$_4$H$_9$)$_4$ and SiO$_2$ and Based On Isol. Active Centres", *Angew. Chem.* 101, (1989) Nr. 3, 360–63.

Wehner & Gustafson, "Catalytic Hydrog. of Esters Over Pd/ZnO", *Journ. of Catlaysis*, 135, 420–426 (1992).
Lewin et al., "Fiber Chemistry", pp. 8–9 (1985).
Martyn V. Twigg, "Catalyst Handbook", 2nd Ed., p. 54.
Homer Adkins, "Catal. Hydrog. of Esters to Alcoh.", *Organic Reactions*, vol. 8, Chp. 1, pp. 2–27 (1954).
Freifelder, "Catal. Hydrog. in Org. Synth.", pp. 129–151.

*Primary Examiner*—Werren B. Lone
*Attorney, Agent, or Firm*—J. Frederick Thomsen; Harry J. Gwinnell

[57] ABSTRACT

A hydrogenation process is described for the production of a hydroxylic compound selected from alcohols and diols by hydrogenation of a corresponding unsaturated organic compound selected from esters, diesters and lactones which involves use of two hydrogenation zones (11, 36), each containing a charge of a hydrogenation catalyst (12, 37). In a first phase of operation one of the hydrogenation zones (36 or 11) is in standby condition and a stream of hot hydrogen-containing gas is passed therethrough. Meanwhile a vaporous feed stream comprising a hydrogen-containing gas and the unsaturated organic compound to be hydrogenated, e.g. dimethyl 1,4-cyclohexanedicarboxylate, is fed to the active zone (11 or 36). This feed stream can include the gas stream from the first mentioned hydrogenation zone (36 or 11). In a second phase of operation the roles of the reactors (11, 36) are switched so that the zone (36 or 11) previously in reactivation condition becomes the active zone whilst the zone that was formerly active (11 or 36) goes into reactivation condition and its partially deactivated catalyst charge is reactivated by the hot hydrogen-containing gas stream.

18 Claims, 4 Drawing Sheets

U.S. PATENT DOCUMENTS

| | | | |
|---|---|---|---|
| 2,137,407 | 11/1938 | Lazier | 568/864 |
| 2,755,317 | 7/1956 | Kassel | 585/654 |
| 2,818,393 | 12/1957 | Lefrancois et al. | 502/160 |
| 2,830,095 | 4/1958 | Nicolaisen | 570/231 |
| 2,884,450 | 4/1959 | Holmquist | 568/880 |
| 2,901,466 | 8/1959 | Kibler et al. | 568/830 |
| 2,917,549 | 12/1959 | Hasek et al. | 568/830 |
| 3,334,149 | 8/1967 | Akin et al. | 568/830 |
| 4,032,458 | 6/1977 | Cooley et al. | 568/830 |
| 4,052,467 | 10/1977 | Mills et al. | 568/880 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/864 |
| 4,751,334 | 6/1988 | Turner et al. | 568/864 |
| 4,837,368 | 6/1989 | Gustafson et al. | 568/881 |
| 4,929,777 | 5/1990 | Irick, Jr. et al. | 568/864 |
| 4,999,090 | 3/1991 | Tateno et al. | 203/36 |
| 5,030,771 | 7/1991 | Fuhrmann et al. | 568/830 |
| 5,124,435 | 6/1992 | Mori et al. | 528/307 |
| 5,142,067 | 8/1992 | Wegman et al. | 549/326 |
| 5,185,476 | 2/1993 | Gustafson | 568/831 |
| 5,191,091 | 3/1993 | Wegman et al. | 549/326 |

FOREIGN PATENT DOCUMENTS

| | | |
|---|---|---|
| 241760 | 10/1987 | European Pat. Off. . |
| 301853 | 2/1989 | European Pat. Off. . |
| 353990 | 2/1990 | European Pat. Off. . |
| 378756 | 7/1990 | European Pat. Off. . |
| 552463 | 7/1993 | European Pat. Off. . |
| 1276722 | 10/1961 | France . |
| 1144703 | 3/1963 | Germany . |
| 1159925 | 12/1963 | Germany . |
| 2719867 | 11/1978 | Germany . |
| 3843956 | 6/1990 | Germany . |
| 4141199 | 6/1993 | Germany . |
| 988316 | 4/1965 | United Kingdom . |
| 1024318 | 3/1966 | United Kingdom . |
| 1454440 | 11/1976 | United Kingdom . |
| 1464263 | 2/1977 | United Kingdom . |
| 2116552 | 9/1985 | United Kingdom . |
| 2250287 | 6/1992 | United Kingdom . |
| 8203854 | 11/1982 | WIPO . |
| 8603189 | 6/1986 | WIPO . |
| 8607358 | 12/1986 | WIPO . |
| 8800937 | 2/1988 | WIPO . |
| 8900886 | 2/1989 | WIPO . |
| 9008121 | 7/1990 | WIPO . |
| 9101961 | 2/1991 | WIPO . |

PROCESS FOR THE PRODUCTION OF ALCOHOLS AND DIOLS

FIELD OF THE INVENTION

This invention relates to a vapour phase hydrogenation process.

BACKGROUND OF THE INVENTION

Various processes have been described for the production of alcohols and diols by hydrogenation of a corresponding unsaturated organic compound selected from esters, diesters and lactones in the presence of a heterogeneous ester hydrogenation catalyst. Such unsaturated organic compounds are unsaturated by virtue of their possessing a carbon-to-oxygen double bond in the linkage —(CO)—O—. They do not need to possess any further unsaturated linkages. Hydrogenation processes of this type are thus applicable to a wide variety of esters, diesters and lactones which contain no unsaturation apart from the afore-mentioned carbon-to-oxygen double bond, for example monoesters of $C_8$ to $C_{22}$ alkylcarboxylic acids, diesters of $C_4$ to $C_{16}$ dicarboxylic acids, and lactones of hydroxycarboxylic acids containing 4 to 16 carbon atoms. However, the presence of further unsaturation in the molecule is not excluded. Thus there can also be used in such processes esters, diesters and lactones which contain further unsaturation in the molecule, for example monoesters of unsaturated $C_8$ to $C_{22}$ aliphatic carboxylic acids, diesters of unsaturated aliphatic or alicyclic carboxylic acids, and unsaturated lactones.

Examples of such hydrogenation processes, many of which are conventionally conducted in the liquid phase, include hydrogenation of alkyl esters of aliphatic monocarboxylic acids to alkanols, and of dialkyl esters of aliphatic dicarboxylic acids to aliphatic diols. It has also been proposed in some cases to effect the hydrogenation reaction under vapour phase reaction conditions.

It is known to produce the cycloaliphatic diol cyclohexanedimethanol by hydrogenation of the corresponding cycloaliphatic diester, usually a dialkyl cyclohexanedicarboxylate, which may itself be produced by hydrogenation of the corresponding dialkyl benzenedicarboxylate, for example dimethyl terephthalate.

A commercial hydrogenation catalyst used for hydrogenation of carboxylic acid esters is copper chromite which may optionally be promoted with barium and/or manganese. The use of such a catalyst in a process for the production of butane-1,4-diol is disclosed in EP-A-0143634. In WO-A-82/03854 there is disclosed a process for effecting the hydrogenolysis of carboxylic acid esters which involves the use of a catalyst comprising a reduced mixture of copper oxide and zinc oxide. Other catalysts useful in hydrogenation reactions which may be mentioned are the palladium/zinc-containing catalysts of WO-A-89/00886 and the mixed catalyst systems of EP-A-0241760. Manganese promoted copper catalysts have also been offered for sale as hydrogenation catalysts.

The hydrogenation reactor or reactors may be operated adiabatically or isothermally with external or internal cooling. Adiabatic reactors are used where possible for preference since they are usually cheaper to construct and to operate than an isothermal reactor of shell and tube design.

The hydrogenation of an ester, diester or lactone feedstock is generally an exothermic reaction. In a liquid phase reaction the feedstock is normally diluted with an inert diluent, conveniently with recycled product hydroxylic compound, and the catalyst is wholly wetted with liquid. The diluent acts as a heat sink and helps to prevent the danger of damage to the catalyst due to the exothermic nature of the hydrogenation reaction.

In a typical vapour phase hydrogenation process the unsaturated organic compound, i.e. the ester, diester or lactone, is normally vaporised directly into a hot hydrogen-containing gas to give a vaporous mixture, which may be heated further or diluted with more hot hydrogen-containing gas in order to raise its temperature above the dew point. It is normally essential to ensure that the vaporous mixture in contact with the catalyst is above its dew point, i.e. above that temperature at which a mixture of gases and vapour just deposits liquid as a fog or a film. This dew point liquid will normally contain all the condensable components of the vapour phase, as well as dissolved gases, in concentrations that satisfy the usual vapour/liquid criteria. It may include the starting material, an intermediate product, a by-product and/or the final hydrogenation product. Generally the process is operated so that the temperature of the vaporous feed mixture is above its dew point, for example about 5° C. to about 10° C. above its dew point. Moreover it is desirable to prevent contact of droplets of liquid with the catalyst, particularly droplets which are rich in the unsaturated organic compound, because damage to the catalyst may result from loss of mechanical strength, from formation of hot spots on the surface of the catalyst or in the pores of the catalyst, due to the exothermic nature of the reaction, leading possibly to sintering and thereby to loss of chemically effective catalyst surface area (particularly in the case of copper-containing catalysts), or from disintegration of the catalyst pellets possibly as a result of explosive vaporisation within the pores of the pellets. Hydrogenation reactor conditions which aim to prevent premature degradation of the hydrogenation catalyst by mechanisms such as the formation of hot spots on the catalyst surface are described in WO-A-91/01961.

Notwithstanding the precautions which may be taken, as described for example in WO-A-91/01961, to maximise the active life of a hydrogenation catalyst, it is still recognised in the art that a hydrogenation catalyst is generally subjected to conditions in the hydrogenation zone which lead inexorably to significant deactivation, and possibly also to irreversible loss of catalytic activity, over a period of time. Such deactivation may be ascribed to different causes in different hydrogenation reactions. For example deposition of carbon or carbonaceous materials on the catalyst surface may be a cause of loss of catalyst activity. In addition to such deactivation processes the catalyst pellets may disintegrate physically in the course of time leading to formation of fines which tend to block the pathway for vapour through the catalyst bed and to lead to an unacceptable increase in pressure drop across the catalyst bed. The deactivation processes may be slowed but not readily reversed.

In any commercial hydrogenation process, the catalyst will eventually lose activity and/or selectivity and need to be replaced with a fresh charge of catalyst. There may be many unrelated but complementary causes of catalyst deactivation in a hydrogenation reaction. These may include i) deposition of carbonaceous materials on the catalyst surface, ii) comminution or structural deterioration of the catalyst pellets resulting from localised physical conditions, iii) poisoning of the catalyst, particularly by compounds containing chlorine or sulphur atoms, and iv) sintering of the catalyst, particularly when the catalyst is a copper-containing catalyst, at high temperatures, for example at temperatures greater than about 230° C.

It is generally recognised in the art that, in hydrogenation reactions utilising copper-containing catalysts, the catalyst is readily deactivated due, it is thought, to sintering or due to migration of metal and is also prone to physical loss of strength such that the catalyst granules tend to disintegrate into a fine powder. Thus it is regarded that catalyst deactivation of copper-containing hydrogenation catalysts is irreversible. Thus, for example, attempts to reactivate copper-containing catalysts which have undergone deactivation as result of prolonged use in the liquid phase hydrogenation of dimethyl 1,4-cyclohexanedicarboxylate according to the teachings of U.S. Pat. No. 3,334,149 have not been successful.

Any hydrogenation process which permits reversal or deceleration of deactivation processes is likely to have significant commercial advantages over the processes taught in the prior art due to lower catalyst consumption costs. Such a process would further provide significant environmental benefits resulting from a reduction in catalyst turnover.

SUMMARY OF THE INVENTION

It is therefore an object of the present invention to provide a process for reactivation of an ester hydrogenation catalyst after it has suffered a loss of catalytic activity during a period of use in the hydrogenation of an ester, diester, or lactone. It is further an object of the present invention to provide a process for hydrogenating an unsaturated organic compound selected from esters of $C_8$ to $C_{22}$ monocarboxylic acids, diesters of dicarboxylic acids, and lactones, to produce a corresponding alcohol or diol, wherein the life of the copper-containing catalyst used therein may be prolonged by its periodic reactivation.

According to the present invention there is provided a process for the production of a hydroxylic compound selected from alcohols and diols by hydrogenation of a corresponding unsaturated organic compound selected from esters, diesters and lactones which comprises:

(a) providing at least two hydrogenation zones, each containing a charge of a granular hydrogenation catalyst effective for catalysing the hydrogenation of the unsaturated organic compound to the hydroxylic compound;

(b) supplying to at least one of the hydrogenation zones, in a first phase of operation, a vaporous feed stream comprising a hydrogen-containing gas and the unsaturated organic compound;

(c) maintaining the at least one hydrogenation zone, in the first phase of operation, under temperature and pressure conditions conducive to hydrogenation of the unsaturated organic compound to yield the hydroxylic compound;

(d) recovering from the at least one hydrogenation zone, in the first phase of operation, a reaction product stream comprising the hydroxylic compound;

(e) supplying to at least one other hydrogenation zone, in the first phase of operation, a stream of hydrogen-containing gas thereby to reactivate the charge of hydrogenation catalyst therein;

(f) supplying to the at least one other hydrogenation zone, in a second phase of operation, a vaporous feed stream comprising a hydrogen-containing gas and the unsaturated organic compound;

(g) maintaining the at least one other hydrogenation zone, in the second phase of operation, under temperature and pressure conditions conducive to hydrogenation of the unsaturated organic material to the hydroxylic compound;

(h) recovering from the at least one other hydrogenation zone, in the second phase of operation, a reaction product stream comprising the hydroxylic compound; and (i) supplying to the at least one hydrogenation zone, in the second phase of operation, a stream of hydrogen-containing gas thereby to reactivate the charge of hydrogenation catalyst therein.

The process of the invention can be used for effecting hydrogenation of essentially any vaporisable ester, diester or lactone that has an appreciable vapour pressure, e.g. about 0.01 psia (about 0.001 bar) or more, at the feed temperature to the respective hydrogenation zone or zones, and that does not deposit elemental carbon on the catalyst. As will be appreciated by those skilled in the art, the invention does not rely on the discovery of any new hydrogenation reaction, of any new hydrogenation conditions, or of any new catalyst but is instead concerned with the physical arrangement and control of the hydrogenation plant and with the overall flow of materials through the two or more hydrogenation zones present in the plant.

Typically the ester, diester or lactone contains up to about 30 carbon atoms.

The unsaturated organic compound is preferably selected from monoesters of $C_8$ to $C_{22}$ alkylcarboxylic acids, diesters of $C_4$ to $C_{16}$ dicarboxylic acids, and lactones of hydroxycarboxylic acids containing 4 to 16 carbon atoms, as well as monoesters of unsaturated $C_8$ to $C_{22}$ aliphatic carboxylic acids, diesters of unsaturated aliphatic or alicyclic carboxylic acids, and unsaturated lactones.

Examples of hydrogenation reactions involving the use as feedstock of an ester, diester or lactone, to which the teachings of the present invention can be applied include the processes taught in WO-A-91/01961, in EP-A0143634, in WO-A-86/03189, and in WO-A-86/07358.

The unsaturated organic compound may be a di-($C_1$ to $C_4$ alkyl) ester of a dicarboxylic acid containing at least 4 carbon atoms. Thus in one preferred process the unsaturated organic compound is a dialkyl ester of a $C_4$ dicarboxylic acid, for example, a dialkyl maleate, and the corresponding hydrogenation product is butane-1,4-diol, gamma-butyrolactone or tetrahydrofuran or a mixture of two or more thereof. In such a process the copper-containing catalyst is preferably a reduced copper chromite catalyst, a reduced promoted copper chromite catalyst, or a reduced manganese promoted copper catalyst. The dialkyl maleate normally is a di-($C_1$ to $C_4$ alkyl) maleate and is preferably dimethyl maleate or diethyl maleate.

A similar reaction is the hydrogenation of gamma-butyrolactone to yield butane-1,4-diol or the hydrogenation of epsilon-caprolactone to yield hexane-1,6-diol.

The unsaturated organic compound may be a di-($C_1$ to $C_4$ alkyl) cyclohexanedicarboxylate, for example dimethyl cyclohexanedicarboxylate, while the hydrogenation product is cyclohexanedimethanol. Thus in a particularly preferred process the unsaturated organic compound is dimethyl 1,4-cyclohexanedicarboxylate and the hydrogenation product is 1,4-cyclohexanedimethanol. Other reactions to which the process of the invention is applicable include hydrogenation of a di-($C_1$ to $C_4$ alkyl) 1,2- or 1,3-cyclohexanedicarboxylate, for example dimethyl 1,2- or 1,3-cyclohexanedicarboxylate, to 1,2- or 1,3-cyclohexanedimethanol respectively.

As another type of unsaturated organic compound which can be used as starting material in the process of the present invention there can be mentioned esters, for example $C_1$ to $C_4$ alkyl esters, of $C_8$ to $C_{22}$ monocarboxylic acids. Typical esters include the methyl and ethyl esters of $C_8$ to $C_{22}$ alkylcarboxylic acids, such as methyl laurate, methyl oleate, methyl stearate, methyl linoleate and the like.

The granular catalyst used in the process of the invention may be any copper-containing catalyst capable of catalysing hydrogenation or hydrogenolysis of an ester to the corresponding alcohol or mixture of alcohols. It may be formed into any suitable shape, e.g. pellets, rings or saddles.

Typical copper-containing ester hydrogenation catalysts include copper-on-alumina catalysts, reduced copper oxide/zinc oxide catalysts, with or without a promoter, manganese promoted copper catalysts, and reduced copper chromite catalysts, with or without a promoter. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Any recognised supporting medium may be used to provide physical support for the copper-containing catalyst used in the process of the invention. This support can be provided by materials such as zinc oxide, alumina, silica, alumina-silica, silicon carbide, zirconia, titania, carbon, a zeolite, or any suitable combination thereof.

The copper-containing catalysts that are particularly preferred for use in the process of the invention are the reduced forms of the copper chromite, promoted copper chromite, and manganese promoted copper catalyst precursors described hereinabove.

In steps (e) and (i) of the process of the invention a respective charge of hydrogenation catalyst is treated with a stream of hydrogen-containing gas thereby to reactivate the catalyst charge. Normally it will be preferred to carry out these steps at elevated temperatures, typically at a temperature of about 150° C. or more up to about 350° C. In these steps the feed temperature to the respective hydrogenation zone or zones may be lower than, e.g. about 10° C. to about 50° C. lower than, substantially equal to, or higher than, e.g. about 10° C. to about 50° C. higher than, the feed temperature to the hydrogenation zone of the vaporous feed stream of steps (b) and (f). Preferably the feed temperature to the hydrogenation zone during the reactivation steps (e) and (i) is within about 30° C. from the feed temperature to the hydrogenation zone of the vaporous feed stream used in steps (b) and (f). Thus during the reactivation steps (e) and (i) the feed temperature may be from about 10° C. to about 30° C. lower than, or from about 10° C. to about 30° C. higher than, the feed temperature to the hydrogenation zone of the vaporous feed stream used in steps (b) and (f).

The stream of hydrogen-containing gas used in step (e) or step (i) may comprise a hot stream of recycle gas. Conveniently the stream of hydrogen containing gas of at least one of steps (e) and (i) comprises a hot stream of recycle and make-up gas.

The feed pressure during step (e) or step (i) can be the same as, lower than, or higher than the feed pressure used in step (b) or step (f). Conveniently it is substantially the same as the feed pressure used in step (b) or in step (f).

In one form of the process of the invention there is recovered from at least one of steps (e) and (i) a stream of hydrogen-containing gas which is admixed with a vaporous hydrogen-containing stream of the unsaturated organic compound to form the vaporous stream of the corresponding one of steps (b) and (f).

In another form there is recovered from at least one of steps (e) and (i) a stream of hydrogen-containing gas which is admixed with the reaction product stream of the corresponding one of steps (d) and (h).

In a still further form of the process there is recovered from at least one of steps (e) and (i) a stream of hydrogen-containing gas which is used to vaporise the unsaturated organic compound and to form a vaporous hydrogen-containing stream of the unsaturated organic compound.

It is further convenient to form the vaporous feed stream of at least one of steps (b) and (f) by admixing hot recycle gas with a vaporous hydrogen-containing stream of unsaturated organic compound.

The direction of flow of the stream of hydrogen-containing gas through the respective hydrogenation zone or zones in at least one of steps (e) and (i) may be the same as, or opposite to, the direction of flow of the vaporous feed stream through that zone in the corresponding one of steps (b) and (f). It will usually be convenient to operate under conditions such that the vaporous hydrogen-containing stream of the unsaturated organic compound is substantially saturated with the unsaturated organic compound.

Preferably the vaporous feed stream of step (b) and/or of step (f) is at a temperature at least about 5° C. above its dew point.

The hydrogenation zones may comprise shell-and-tube reactors which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such adiabatic reactors may each contain a single charge of a hydrogenation catalyst or may contain two or more beds of catalyst, or beds of different hydrogenation catalysts. If desired, external or internal inter-bed heat exchangers may be provided in order to adjust the feed temperature to one or more beds of catalyst downstream from the inlet to the respective adiabatic hydrogenation reactor.

In the process of the invention there can be used two or more hydrogenation zones in parallel, at least one of which is at any time on line and the other or others of which is or are in reactivation mode. When there are only two zones then one zone will be on line while the other is in reactivation mode. If the plant has three or more zones, then one or more of the zones will usually be in reactivation mode, while one or more others is or are on line. Alternatively, if the plant has three or more zones, then at least one zone can be on line, at least one zone can be in standby mode, and at least one zone is in reactivation mode. The number of zones on line and in reactivation or standby mode at any given time will depend on the desires of the plant operator and upon the economic considerations associated with the particular hydrogenation reaction in question.

In a vapour phase hydrogenation process, which is typically strongly exothermic, it is important to ensure that the unsaturated organic compound is above its dew point, and hence in vapour form rather than in liquid form, in the vaporous hydrogen-containing reaction mixture whilst it is in contact with the hydrogenation catalyst. In this way the risk of droplets of a liquid phase rich in unsaturated organic compound contacting the catalyst and the resulting localised development of "hot spots" and the risk of formation of "fines" due to explosive localised vaporisation of liquid within the pores of the catalyst are minimised. In some cases, however, particularly when the hydrogenation product is significantly less volatile than the unsaturated organic compound, condensation on the catalyst of a liquid phase which is rich in the hydrogenation product can be tolerated. Hence in some cases, as for example in the catalytic vapour phase hydrogenation of dimethyl 1,4-cyclohexanedicarboxylate to yield 1,4-cyclohexanedimethanol, it is not essential that the reaction product mixture at the downstream end of the catalyst bed shall necessarily be above the dew point of the hydrogenation product. Hence, although vapour phase conditions are required at the inlet end of the catalyst bed with the unsaturated organic compound above its dew point, mixed vapour-liquid conditions are permissible at the exit end of the catalyst bed. This is of importance in hydrogenation processes in which the product, e.g. 1,4-cyclohexanedimethanol, is considerably less volatile than the unsaturated organic compound starting material, such as dimethyl 1,4-cyclohexanedicarboxylate. In such a process the gas:unsaturated organic compound molar ratio should be high enough to maintain the vaporous feed stream above its dew point but does not need to be so high as to maintain the reaction product stream at the exit end of the catalyst bed above its dew point. This has a significant effect on the size and running costs of the plant since the quantity of circulating gas can be reduced, thereby enabling smaller pipework and a smaller gas recycle compressor to be used than would be the case in which the reaction product stream is above its dew point also.

In the vaporous feed stream of step (b) and step (f) the hydrogen-containing gas:unsaturated organic compound molar ratio can vary within wide limits, depending upon the temperature, pressure, and the volatility of the unsaturated organic compound. Although the major gaseous constituent is hydrogen, other gases may also be introduced, normally in minor amount, in the hydrogen-containing gas supplied as make-up gas to the process, such as nitrogen, argon, methane, and carbon oxides. The less volatile that the unsaturated organic compound is the lower will be its vapour pressure at a given temperature and the higher the hydrogen-containing gas:unsaturated organic compound molar ratio will have to be in order to keep the vaporous feed mixture above its dew point at the relevant temperature. Conversely the more volatile that the unsaturated organic compound is the lower that this molar ratio need be. Usually it will range from about 10:1 up to 8000:1, preferably in the range of from about 200:1 to about 1000:1.

The hydrogen-containing gas used in steps (b), (e), (f), and (i) of the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. For example, in the hydrogenation of dimethyl cyclohexanedicarboxylate using gas recycle, the gas recycle stream will contain minor amounts of methanol.

Although the process of the invention is operated with the feed stream in the vapour phase, it is convenient to express the feed rate of the unsaturated organic compound to the hydrogenation zone as a space velocity and to express that space velocity as a liquid hourly space velocity. Hence it is convenient to express the feed rate in terms of the ratio of the liquid feed rate of the unsaturated organic compound to the vaporisation zone to the volume of the hydrogenation catalyst. Thus the equivalent liquid hourly space velocity of the unsaturated organic compound through the hydrogenation catalyst is preferably from about 0.05 to about 4.0 $h^{-1}$. In other words it is preferred to feed the liquid unsaturated organic compound to the vaporisation zone at a rate which is equivalent to, per unit volume of catalyst, from about 0.05 to about 4.0 unit volumes of unsaturated compound per hour (i.e. about 0.05 to about 4.0 $m^3h^{-1}$ per $m^3$ of catalyst). Even more preferably the liquid hourly space velocity is from about $0.1 \, h^{-1}$ to about $1.0 \, h^{-1}$. If the unsaturated organic compound is a solid at ambient temperatures, then it may be necessary to heat it sufficiently to melt it or to dissolve it in a suitable inert solvent, in which latter case the solvent is ignored for the purpose of measuring the liquid hourly space velocity.

It will be readily apparent to those skilled in the art that the rate of passage of the vaporous feed stream through the hydrogenation zone will depend upon the feed rate of the unsaturated organic compound to the vaporisation zone and upon the hydrogen-containing gas:unsaturated organic compound molar ratio.

In steps (c) and (g) of the process of the invention it is preferred to use a feed temperature which is in the range of from about 150° C. to about 350° C., preferably in the range of from about 150° C. to about 300° C. The precise choice of feed temperature will depend on the stability of the unsaturated organic compound undergoing hydrogenation, the activity of the copper-containing catalyst, and the temperature tolerance of the catalyst. In many cases the most preferred feed temperature range is from about 180° C. to about 250° C. However, in the case of hydrogenation of dimethyl 1,4-cyclohexanedicarboxylate the preferred feed temperature is in the range of from about 200° C. to about 260° C.

The feed pressure is preferably in the range of from about 150 psia (about 10.34 bar) up to about 2000 psia (about 137.90 bar). However, the benefits and advantages of the present low pressure process utilising vaporous feed conditions are best realised by carrying out the process at a pressure of from about 450 psia (about 31.03 bar) up to about 1000 psia (about 68.95 bar).

It appears from our work during investigation of the hydrogenation of dimethyl 1,4-cyclohexanedicarboxylate that an explanation for the decline in catalyst activity is that involatile polymeric byproducts are formed on the copper-containing catalyst surface which are themselves susceptible to hydrogenation or hydrogenolysis. Such polymeric byproducts may be, for example, polyesters formed by ester exchange between the feed unsaturated organic compound and a hydroxylic component, e.g. 1,4-cyclohexanedimethanol or an intermediate product such as methyl 4-hydroxymethylcyclohexanecarboxylate. It can be postulated that the high boiling diester thus formed can then undergo further ester exchange reactions leading to involatile polymeric products. Alternatively ethers and polyethers can be formed by reaction between molecules of 1,4-cyclohexanedimethanol to form di-(4-hydroxymethylcyclohexylmethyl) ether which has itself free hydroxyl groups which can form further ether or ester linkages and yield corresponding involatile polyethers or polyester-polyethers.

Analogous polyester, polyether and mixed polyether-polyester products can be envisaged as being formed during hydrogenation of dimethyl maleate, diethyl maleate, diethyl succinate, or dimethyl fumarate to form butane-1,4-diol, during hydrogenation of gamma-butyrolactone to yield butane-1,4-diol, or during hydrogenation of epsilon-caprolactone to form hexane-1,6-diol.

Such polyester, polyether and mixed polyether-polyester by products are capable of being hydrogenated or undergoing hydrogenolysis. It is consistent with our findings to assume that in the reactivation step (e) such involatile polymeric materials themselves undergo hydrogenation or hydrogenolysis to yield more volatile materials such as 1,4-cyclohexanedimethanol, when dimethyl 1,4-cyclo-hexanedicarboxylate has been hydrogenated, or butane-1,4-diol, when a maleate ester or gamma-butyrolactone has been hydrogenated.

In the hydrogenation of an ester of a long chain fatty acid, for example a methyl ester of a $C_8$ to $C_{22}$ aliphatic monocarboxylic acid, the long chain alcohol formed can undergo ester interchange with the starting material to form a $C_8$ to $C_{22}$ alkyl ester of the $C_8$ to $C_{22}$ monocarboxylic acid. It is postulated that this $C_{16}$ to $C_{44}$ ester, which is much less volatile than either the ester starting material or the desired alcohol product, can eventually form a sufficiently thick liquid film on the catalyst surface to cause significant catalyst deactivation through hindering free access of the ester starting material to the active catalytic sites.

The period required for reactivation will depend upon the nature of the hydrogenation reaction, upon the extent of deactivation of the copper-containing catalyst, and upon the volatility of the products of the reactivation procedure, as well as upon the temperature and hydrogen partial pressure prevailing in the hydrogenation zone during the reactivation step. Typically this period may vary from a few minutes, for example about 10 minutes or less, up to a period of days, for example 10 days or more. Normally it will suffice, assuming that favourable temperature and hydrogen partial pressure conditions have been selected, to carry out reactivation for a matter of a few hours, for example from about 1 hour up to about 24 hours.

DETAILED DESCRIPTION OF THE PREFERRED EMBODIMENTS

Figure 1:
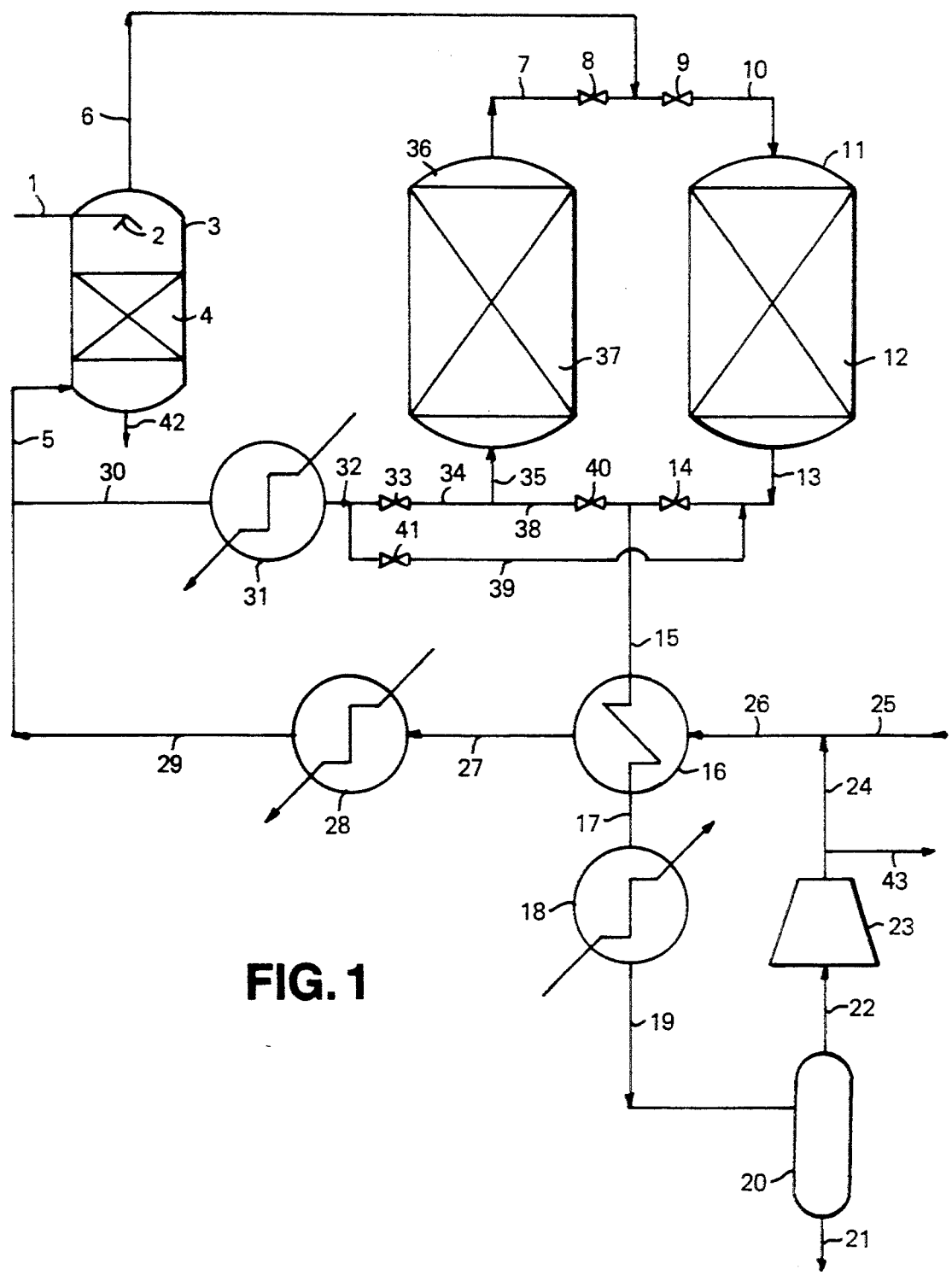
FIGS. 1 to 3 are each a simplified flow diagram of a plant for production of 1,4-cyclohexanedimethanol in two hydrogenation reactors connected in parallel by hydrogenation of dimethyl 1,4-cyclohexanedicarboxylate.

It will further be understood by those skilled in the art that the drawings are diagrammatic and that further items of equipment such as temperature and pressure sensors, pressure relief valves, control valves, level controllers and the like would additionally be required in a commercial plant. The provision of such ancillary items of equipment forms no part of the present invention and is in accordance with conventional chemical engineering practice. Moreover it is not intended that the scope of the invention should be limited in any way by the precise methods of heating, vaporising and condensing various process streams or by the arrangement of heaters, heat exchangers, vaporising or condensing apparatus provided therefor. Any suitable arrangement of equipment other than those depicted in the drawings which fulfils the requirements of the invention may be used in place of the illustrated equipment in accordance with conventional chemical engineering techniques.

Referring to FIG. 1 of the drawings, a technical grade of dimethyl 1,4-cyclohexanedicarboxylate is supplied in line 1, in a first phase of operation, to a vaporiser nozzle 2 located in an upper part of a vaporiser vessel 3 above a bed of packing 4. A stream of hot hydrogen-containing gas is supplied to the bottom of vaporiser vessel 3 in line 5. A saturated vaporous mixture comprising dimethyl 1,4-cyclohexanedicarboxylate is recovered in line 6 from the top of vaporiser vessel 3. The resulting vaporous mixture is mixed with further hot hydrogen-containing gas from line 7 under the control of valve 8. The combined stream which now has a gas:dimethyl 1,4-cyclohexanedicarboxylate molar ratio of about 400:1 and is at a pressure of about 900 psia (about 62.05 bar) and at a temperature of about 230° C., is fed by way of valve 9 and line 10 to a hydrogenation reactor 11 which contains a bed of a pelleted heterogeneous hydrogenation catalyst 12, such as reduced copper chromite or the chromium-free catalyst designated DRD92/89. The hydrogenation reaction product mixture exits reactor 11 via line 13 and passes through valve 14 to enter line 15. The hydrogenation reaction product mixture in line 15 is cooled in heat interchanger 16 and the resulting partially condensed mixture passes on in line 17 through cooler 18 in which it is further cooled. The resulting mixture of gas and condensate flows on in line 19 to a gas-liquid separator 20 from which a mixture of methanol and crude 1,4-cyclohexanedimethanol is recovered in line 21. The uncondensed gaseous mixture in line 22 comprises unreacted hydrogen together with inert gases and methanol vapour and is compressed by means of compressor 23 to give a compressed gas stream in line 24.

The compressed recycled gas in line 24 is combined with make-up hydrogen-containing gas from line 25. The combined mixture in line 26 is heated by passage through heat exchanger 16 and flows on in line 27 to heater 28 in which its temperature is raised further to a suitable temperature for effecting vaporisation of the dimethyl 1,4-cyclohexanedicarboxylate feed. The resulting hot gas in line 29 is then divided into two streams, one being the stream in line 5 and the other being a stream in line 30. This latter stream is heated further in heater 31 to a temperature of about 240° C. and passes on by way of line 32, valve 33 and lines 34 and 35 to the bottom end of a second hydrogenation reactor 36 which, in this first phase of operation, is in reactivation mode. Reactor 36 contains a charge of hydrogenation catalyst 37. The hot gas exiting the top of reactor 36 in line 7 is admixed, as already described above, with the saturated vaporous mixture in line 6 to increase the hydrogen:dimethyl 1,4-cyclohexanedicarboxylate molar ratio therein and to raise its temperature above its dew point, e.g. at least 5° C. to 10° C. above its dew point.

The plant also includes lines 38 and 39 and valves 40 and 41 both of which are closed in this phase of operation. Line 42 indicates a line by means of which a stream containing any "heavies" collecting in the bottom of vaporiser vessel 3 can be drawn off. Reference numeral 43 indicates a purge gas line through which a purge gas stream can be taken in order to limit the build up of inert gases in the circulating gas. Such inert gases may enter the plant in the make up gas stream in line 25.

After a period of operation the activity of the catalyst charge 12 will have declined to a point at which reactivation is desirable. Although the reasons for catalyst deactivation have not been clarified, it can be postulated that a possible cause of this loss of catalyst activity is the formation of traces of involatile polyesters on the catalyst surface due to ester exchange reactions between, for example, dimethyl 1,4-cyclohexanedicarboxylate, on the one hand, and 1,4-cyclohexanedimethanol, or methyl 4-hydroxymethylcyclohexanecarboxylate, which can be postulated to be an intermediate product of the hydrogenation reaction, or hydroxymethylcyclohexylmethyl 1,4-cyclohexanedicarboxylate, which is the ester interchange product between dimethyl 1,4-cyclohexanedicarboxylate and 1,4-cyclohexanedimethanol, on the other hand. The resulting di- or trimeric materials can then undergo further reaction with components of the vaporous mixture to cause these oligomeric chains to grow. Polyethers and mixed polyethers-polyesters can also be formed.

Such polymeric byproducts on the catalyst surface are susceptible to hydrogenation. Hence reactivation of the catalyst by treatment with a hot hydrogen-containing gas is possible. It has further been shown in the course of experimental work to investigate the hydrogenation of dimethyl 1,4-cyclohexanedicarboxylate which forms the background to the present invention that, for whatever reason, the passage of a hot stream of hydrogen-containing gas over partially deactivated catalyst has a beneficial effect in at least partially restoring the activity of the catalyst.

Accordingly in a second phase of operation valve 33 is shut and valve 41 is opened, while valve 14 is closed and valve 40 is opened. In this way hydrogenation reactor 36 with its fresh or reactivated catalyst charge 37 is brought on line, whilst reactor 11 goes into reactivation mode and its partially deactivated charge of catalyst 12 is reactivated. In this second mode of operation the saturated vaporous mixture in line 6 is mixed with hot hydrogen-containing gas from line 10 to form a vaporous feed mixture which flows in line 7 through reactor 36 and its catalyst charge 37. The resulting reaction mixture passes by way of lines 35 and 38 through valve 40 to line 15. The hot hydrogen-containing gas from line 32 passes through valve 41 to line 39 and then through line 13 to the bottom of hydrogenation reactor 11.

When the catalyst charge 37 has become deactivated to some extent the valves 14, 33, 40 and 41 can be readjusted to switch the flows through hydrogenation reactors 11 and 36 back to those of the first phase of operation.

The above described steps can be repeated as often as may be expedient, bringing the reactors 11 and 36 on line in turn until the reactivation procedure no longer results in the desired increase in catalyst activity or until the plant has to be shut down for maintenance or other reasons, whereupon the catalyst charges 12 and 37 can be discharged and replaced by fresh charges of catalyst or catalyst precursor.

The make-up gas in line 25 can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired.

At start up of the plant the reactors 11 and 36 are each charged with a charge of a heterogeneous hydrogenation catalyst precursor, such as a copper chromite catalyst precursor. Preferably, however, the reactors 11 and 36 are charged with a chromium-free hydrogenation catalyst, such as DRD92/89. The catalyst precursor is then reduced carefully following the catalyst supplier's instructions. If the process of EP-A-0301853 is used to reduce a copper chromite precursor, then both beds of catalyst 12 and 37 can be reduced simultaneously. In other cases it may be expedient to reduce the beds 12 and 37 separately. After pre-reduction of the catalyst precursor hot hydrogen-containing gas is circulated through the plant. When the appropriate feed temperatures to vaporiser vessel 3 and to reactor 11 have been achieved the flow of dimethyl 1,4-cyclohexanedicarboxylate in line 1 is commenced to bring the plant on line in the first phase of operation.

Figure 2:
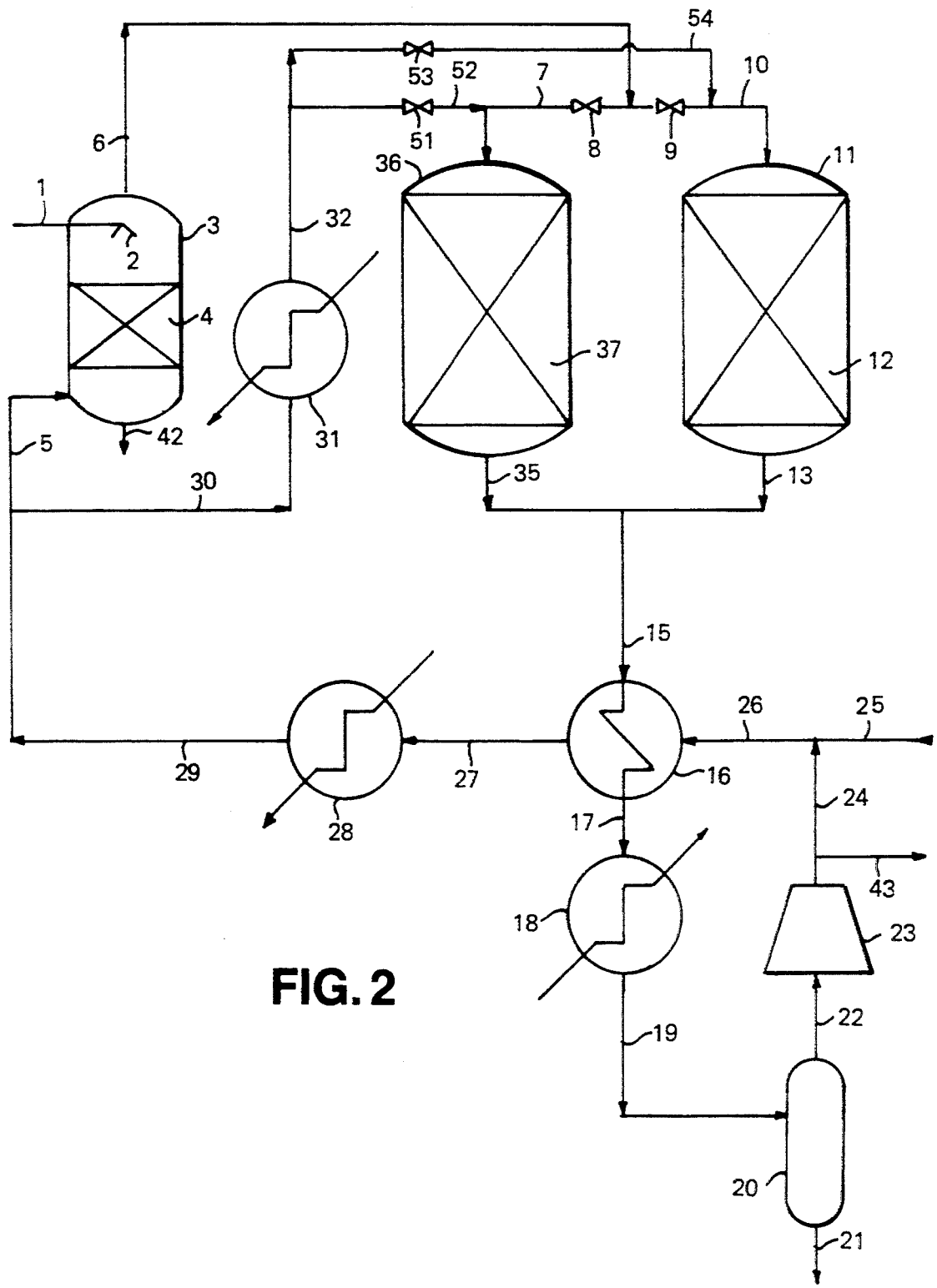

In FIG. 2 of the drawings the same reference numerals have been used as in FIG. 1 to denote like items of equipment. Whereas the hydrogen-containing gas flows in the plant of FIG. 1 through the catalyst bed 12 or 37 in the opposite direction during the reactivation mode from the direction of flow of the vaporous feed stream through the same bed 12 or 37 in the on line mode, in the plant of FIG. 2 the direction of gas flow during the catalyst reactivation mode and that during the on line mode through a particular bed 12 or 37 are the same in each case.

In the plant of FIG. 2 hot gas from the stream in line 32 can be fed either via valve 51 and line 52 into line 7 and then through reactor 36 or via valve 53 and line 54 into line 10 and then through reactor 11. If reactor 11 is in on line mode with valve 8 closed and reactor 36 is in reactivation mode, then valve 51 is adjusted so that most of the gas from line 32 flow through valve 51 into reactor 36 and only sufficient gas passes through valve 53 into line 10 to raise the feed temperature to reactor 11 above its dew point. To bring reactor 36 into on line mode valve 9 is closed and valve 8 is opened, whereupon valve 51 is closed somewhat and valve 53 is opened a corresponding amount to cause most of the gas from line 32 to flow through reactor 11 while only sufficient gas passes through valve 51 to satisfy dew point requirements.

In the plant of FIG. 2 any volatile potential catalyst deactivating materials released in the reaction mode do not pass through the on line catalyst charge and can be recovered in the product stream in line 21. Although preliminary indications are that no such catalyst deactivating materials are released when the unsaturated organic compound being hydrogenated is dimethyl 1,4-cyclohexanedicarboxylate, this may not be the case when other unsaturated organic compounds are being hydrogenated.

Figure 3:
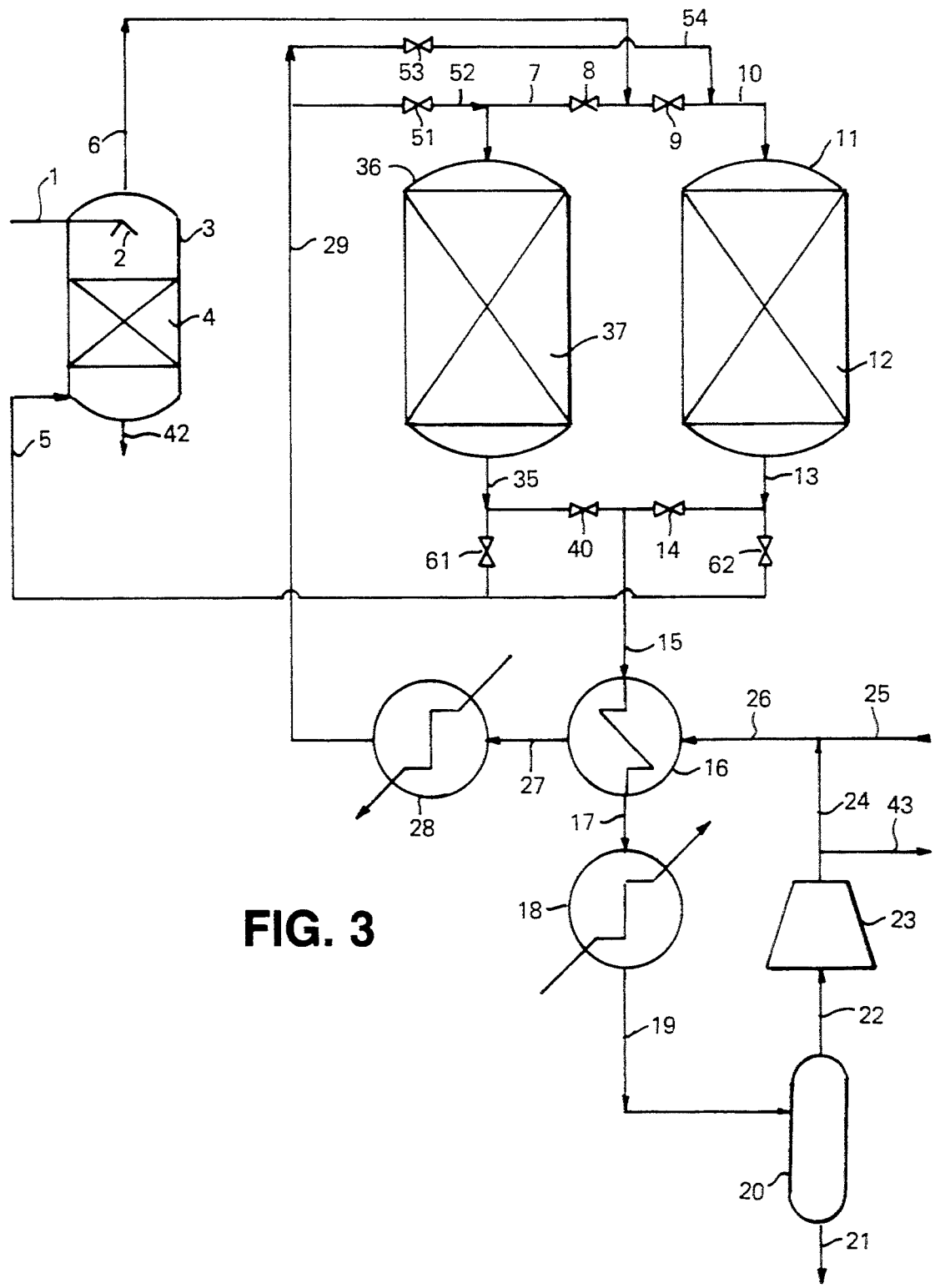

FIG. 3 illustrates a further design of hydrogenation plant in accordance with the invention. In this plant, as in the plant of FIG. 2, the direction of gas flow through each of the catalyst beds 12 and 37 during its respective reactivation mode is the same as the direction of flow of vaporous feed mixture during its on line mode. The reference numerals used in FIG. 3 indicate the same items of equipment that appear in FIG. 1 and also in FIG. 2.

In the plant of FIG. 3 the hydrogen-containing gas supplied in line 5 for vaporisation of the incoming dimethyl 1,4-cyclohexanedicarboxylate feed in line 1 is passed first through one of the catalyst beds 12 or 37 in its respective reactivation mode. Hence, when reactor 36 is in reactivation mode, most of the hot gas in line 29 is fed through valve 51 and line 52 into reactor 36 through catalyst charge 37, and passes out via line 35 and valve 61 to line 5. Valves 8 and 40 are closed and valve 53 is open only so far as is necessary to permit passage of sufficient gas into line 10 to satisfy dew point requirements. Meanwhile the vaporous feed mixture in line 6 passes through valve 9 and via line 10 into reactor 11 whose catalyst charge 12 is in on line mode. The product stream in line 13 flows through valve 14 into line 15, valve 62 being closed. When it is desired to bring catalyst charge 37 on line and to reactivate catalyst charge 12 in reactor 11, valves 8, 40 and 62 are opened, while formerly open valves 9, 14 and 61 are closed. Valve 53 is opened somewhat and the gas flow through valve 51 is reduced to the extent necessary for dew point considerations. To revert to the former condition with catalyst charge 37 being reactivated and catalyst charge 12 being on line again, the conditions of the various valves are each readjusted to its respective former condition. This procedure can be repeated one or more further times as may be expedient bringing the reactors 11 and 36 on line in turn until the reactivation procedure no longer results in the desired increase in catalyst activity or until the plant has to be shut down for maintenance or other reasons, whereupon the catalyst charges 12 and 37 can be discharged and replaced by fresh charges of catalyst or catalyst precursor.

It will be understood by those skilled in the art that, whilst dimethyl 1,4-cyclohexanedicarboxylate has been chosen as a suitable material with which to exemplify the process of the invention, the process of the invention is by no means limited in its application to hydrogenation reactions involving dimethyl 1,4-cyclohexanedicarboxylate and may, in fact, be applied to many vapour phase hydrogenation reactions using esters, diesters or lactones as feedstocks, in which involatile hydrogenatable byproducts are formed and deposited on the catalyst surface, for example hydrogenation of dimethyl or diethyl maleate to yield butane-1,4-diol.

The invention is further described with reference to the following Examples. The compositions of copper-containing catalysts A and B used in the Examples are listed in Table I. The oxygen content of the catalyst has been omitted in each case.

TABLE I

| | | Composition wt % | | | | | | Surface area | Density | Pore Volume |
| | Catalyst | Cu | Cr | Zn | Mn | Ba | Al | m$^2$/g | g/cm$^3$ | mm$^3$/g |
| --- | --- | --- | --- | --- | --- | --- | --- | --- | --- | --- |
| A | DRD89/21 | 57.6 | 19.0 | <0.01 | 0.09 | <0.01 | <0.01 | 28 | 1.420 | 200 |
| B | DRD92/89 | 41.1 | 0.26 | <0.01 | 6.4 | <0.01 | 20.4 | 47.1 | 1.452 | 211 |

EXAMPLES 1 to 7

Figure 4:
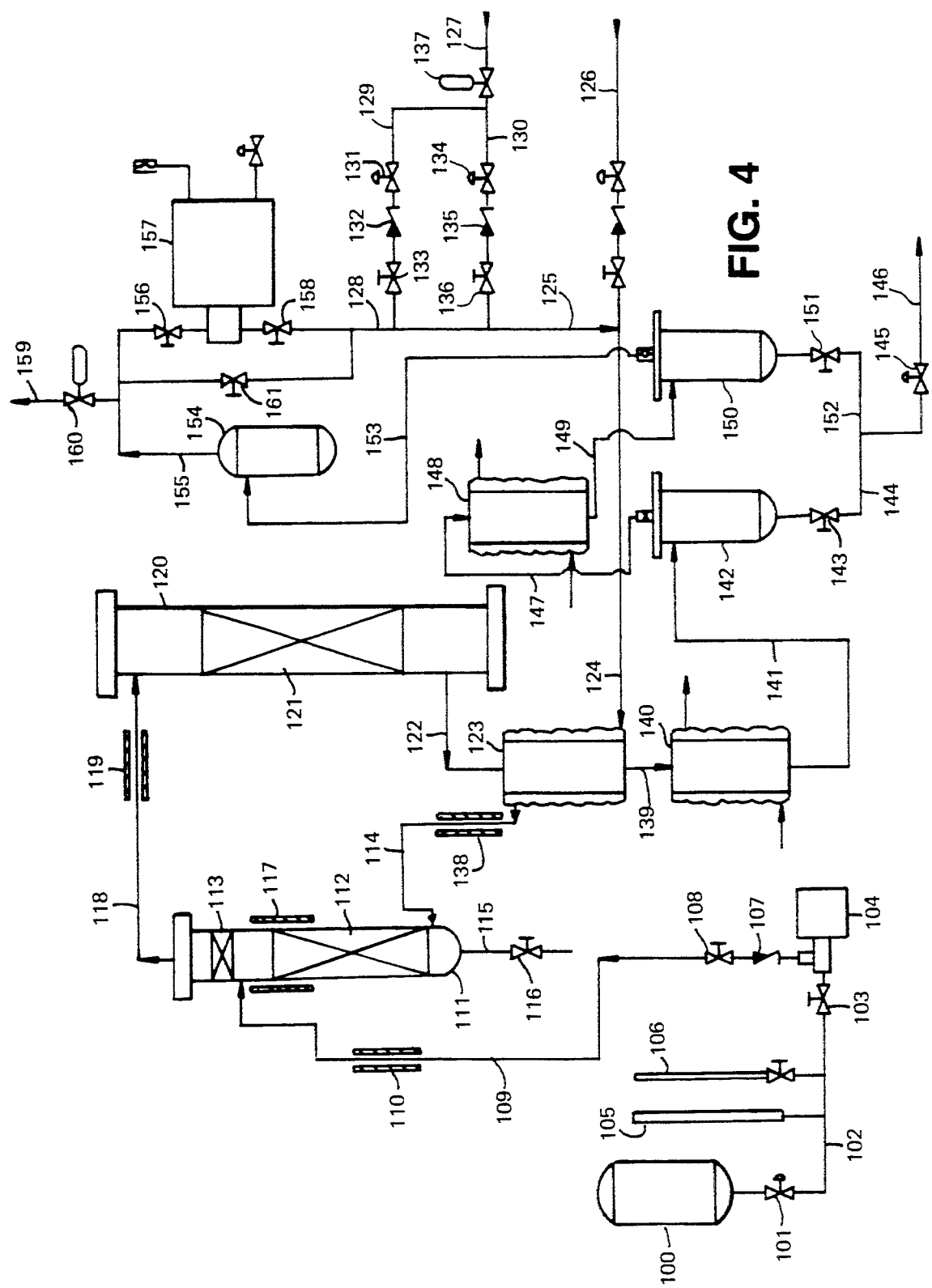
FIG. 4 is a simplified flow diagram of an experimental apparatus for production of 1,4-cyclohexanedimethanol in a single hydrogenation zone by hydrogenation of dimethyl 1,4-cyclohexanedicarboxylate.

The hydrogenation of a technical grade of dimethyl 1,4-cyclohexanedicarboxylate was investigated using the experimental apparatus illustrated in FIG. 4.

The composition of the technical grade feed was: 34.47 wt % trans-dimethyl 1,4-cyclohexanedicarboxylate, 62.61 wt % cis-dimethyl 1,4-cyclohexanedicarboxylate, 1.50 wt % methyl hydrogen 1,4-cyclohexanedicarboxylate of formula

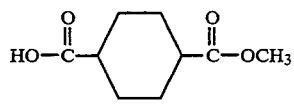

and 0.05 wt % water, with the balance being impurities including di-4-hydroxymethylcyclohexylmethyl ether of formula

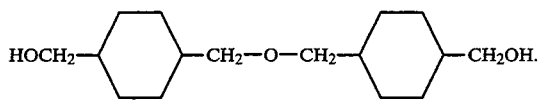

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous mixture supplied to the hydrogenation zone in a commercial plant will generally contain methanol in addition to hydrogen and an unsaturated organic compound. In order that the experimental rig described hereinbelow should accurately predict the results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In these Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 4. An approximately 70 wt % solution of the technical grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm × 6 mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 300 ml (428.1 g) of a pelleted copper chromite hydrogenation catalyst 121. The catalyst was catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) embedded within insulation around reactor 120 under the control of appropriately positioned thermocouples (not shown). The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of copper-containing catalyst was placed in reactor 120 which was then purged with nitrogen. The catalyst charge was then reduced according to the teachings of EP-A-0301853.

Technical grade dimethyl 1,4-cyclohexanedicarboxylate, appropriately diluted with methanol, was then pumped to the vaporiser 111 at a feed rate corresponding to an appropriate liquid hourly space velocity. The feed temperature, feed pressure and gas:dimethyl 1,4-cyclohexanedicarboxylate molar ratio in the vaporous mixture in line 118 were selected so that the hydrogenation zone was operated under conditions which prevented the condensation of both dimethyl 1,4-cyclohexanedicarboxylate and the less volatile 1,4-cyclohexanedimethanol product. The temperature in the hydrogenation zone was above the dew point of the vaporous feed mixture at the operating pressure.

The liquid in line 146 was analysed periodically by capillary gas chromatography using a 15 m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. Operation of the rig was monitored over a period of several weeks. From the results obtained it appeared that over this period dimethyl 1,4-cyclohexanedicarboxylate had been converted in excess of 99%, with a selectivity to 1,4-cyclohexanedimethanol of approximately 98.5% being obtained, the balance being minor by-products. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction.

After further operation of the rig the conversion of dimethyl 1,4-cyclohexanedicarboxylate was found to be 97.53% under the conditions specified for Example 1 in Table II below, the selectivity to 1,4-cyclohexanedimethanol being 96.89%. The operating conditions were subsequently altered to those listed under Example 2 in Table II. Operation of the rig was continued for a number of days over the course of which it was necessary to raise the feed temperature by 3° C. in order to maintain the desired conversion of dimethyl 1,4-cyclohexanedicarboxylate. The results observed are listed under Example 3 in Table II. A further period of continuous operation of the rig ensued during which the activity declined over the course of several weeks, as evidenced by the increase in feed temperature of 6° C., compared with Example 2, necessary to maintain the conversion of dimethyl 1,4-cyclohexanedicarboxylate as near as possible the desired value. The results at this time are given under Example 4. Operation was continued for a few days more. Then the conditions were changed to those set out in Table II under Example 5, which are comparable to those specified for Example 1. Compared with Example 1 the conversion had dropped over the intervening period of operation from 97.53% to 85.47%, thus demonstrating that a very significant loss of catalyst activity had occurred. The dimethyl 1,4-cyclohexanedicarboxylate feed was then turned off and, after an interval of approximately 3 hours, the feed temperature to reactor 120 was increased to 250° C. and hydrogen gas was passed through the reactor 120 at this temperature for 14 hours in order to effect catalyst reactivation. The reactor 120 was then returned to the same conditions as those which prevailed immediately prior to the reactivation step. The dimethyl 1,4-cyclohexanedicarboxylate conversion immediately after catalyst reactivation had occurred was 91.86% as reported in Example 6, demonstrating that at least partial reactivation had been successfully accomplished. This was confirmed by restoring the operating conditions substantially to those of Example 4. The conversion had been increased from 98.61%, as reported in Example 4, to 99.79%, as reported in Example 7, at a feed temperature of 236° C.

Comparison of Examples 1, 5 and 6 shows that in the interval between Examples 1 and 5 the catalyst had dropped in activity from an arbitrary relative activity value of 100% in Example 1, as measured by conversion of dimethyl 1,4-cyclohexanedicarboxylate, to a relative catalyst activity of 87.63%, measured on the same basis in Example 5. After the reactivation procedure the relative catalyst activity, as reported in Example 6, had been restored to 94.19% of the original value.

TABLE II

| Example No. | Inlet Temp. °C. | Gas:DMCD Molar ratio | LHSV $h^{-1}$ | Pressure psia (bar) | DMCD conversion mol % | Selectivity mol % | | | |
|---|---|---|---|---|---|---|---|---|---|
| | | | | | | CHDM | BYPR | METH | DETH |
| 1 | 220 | 691 | 0.42 | 900 (62.05) | 97.53 | 96.89 | 2.75 | 0.14 | 0.14 |
| 2 | 230 | 381 | 0.31 | 903 (62.26) | 98.99 | 96.50 | 3.20 | 0.19 | 0.11 |
| 3 | 233 | 340 | 0.31 | 903 (62.26) | 99.06 | 96.54 | 3.16 | 0.19 | 0.11 |
| 4 | 236 | 354 | 0.30 | 906 (62.47) | 98.61 | 96.46 | 3.24 | 0.21 | 0.09 |
| 5 | 220 | 716 | 0.42 | 900 (62.05) | 85.47 | 96.63 | 3.15 | 0.11 | 0.11 |
| 6 | 219 | 715 | 0.41 | 900 (62.05) | 91.86 | 96.78 | 2.85 | 0.11 | 0.17 |

TABLE II-continued

| Example No. | Inlet Temp. °C. | Gas:DMCD Molar ratio | LHSV h$^{-1}$ | Pressure psia (bar) | DMCD conversion mol % | Selectivity mol % | | | |
|---|---|---|---|---|---|---|---|---|---|
| | | | | | | CHDM | BYPR | METH | DETH |
| 7 | 236 | 330 | 0.29 | 901 (62.12) | 99.79 | 95.74 | 3.84 | 0.24 | 0.18 |

Notes to Table II:
DMCD = dimethyl 1,4-cyclohexanedicarboxylate
LHSV = liquid hourly space velocity
CHDM = 1,4-cyclohexanedimethanol
BYPR = miscellaneous byproducts
METH = 4-methoxymethyl cyclohexanemethanol
DETH = di-(4-hydroxymethylcyclohexylmethyl) ether
Gas = hydrogen containing gas containing more than 98% hydrogen.

EXAMPLES 8 to 12

The general procedure of Examples 1 to 7 is repeated using dimethyl maleate, diethyl, maleate, diethyl succinate, dimethyl fumarate, or gamma-butyrolactone in place of dimethyl 1,4-cyclohexane-dicarboxylate, resulting in each case in production of butane-1,4-diol. A similar improvement in catalyst activity is observed following the reactivation procedure.

EXAMPLE 13

The general procedure of Examples 1 to 7 is repeated except that catalyst A is replaced by catalyst B with similarly good results.

EXAMPLE 14

An experimental rig is designed for use in a process intended to be operated in a plant of the type depicted in FIG. 1. This rig is essentially identified to that of FIG. 4 except that reactor 120 is replaced by a pair of reactors in series. The same general procedure is followed as described in respect of Examples 1 to 7, with a first reactor on line and maintained under conditions effective to hydrogenate the vaporous feed mixture supplied thereto and a second reactor in standby or reactivation mode with no hydrogenarable material supplied thereto. A gradual deactivation of the catalyst charge contained within the first reactor is observed, substantially as exemplified in Examples 1 to 7. In order to reactivate the catalyst charge within the first reactor, the vaporous feed mixture supplied thereto is diverted into the second reactor, thereby to allow continuation of the hydrogenation reaction in the second reactor. Meanwhile, the first reactor is supplied with a hydrogen-containing gas thereby to reactivate the catalyst charge therein. After a period of operation during which the catalyst activity in the second reactor declines in a manner similar to the deactivation of the catalyst within a single hydrogenation reactor recorded in Examples 1 to 7, the vaporous feed mixture is switched back to the first reactor thereby to allow continuation of the hydrogenation reaction whilst the reactivation procedure is performed on the second reactor. The activity of the hydrogenation catalyst in the first reactor is seen to be significantly increased in a manner similar to that reported for a single hydrogenation zone. The overall procedure is repeated several times with excellent maintenance of conversion of dimethyl 1,4-cyclohexanedicarboxylate.

We claim:

1. A process for the production of alcohols and diols by hydrogenation of a corresponding unsaturated organic compound selected from esters, diesters and lactones which comprises:
   (a) providing at least two hydrogenation zones, each containing a charge of a granular hydrogenation catalyst effective for catalysing the hydrogenation of the unsaturated organic compound to the alcohol or diol and selected from copper-containing and Group VIII metal-containing catalysts;
   (b) supplying to at least one of the hydrogenation zones, in a first phase of operation, a vaporous feed stream comprising a hydrogen-containing gas and an unsaturated organic compound selected from $C_1$ to $C_4$ alkyl esters of $C_8$ to $C_{22}$ alkylcarboxylic acids, di-($C_1$ to $C_4$) alkyl diesters of $C_4$ to $C_{16}$ dicarboxylic acids, gamma-butyrolactone and epsilon-caprolactone;
   (c) maintaining the at least one hydrogenation zone, in the first phase of operation, at a temperature in the range of from about 150° C. to about 350° C. and a pressure in the range of from about 150 psia up to about 2000 psia;
   (d) recovering from the at least one hydrogenation zone, in the first phase of operation, a reaction product stream comprising the alcohol or diol;
   (e) supplying to at least one other hydrogenation zone, in the first phase of operation, a stream of hydrogen-containing gas thereby to reactivate the charge of hydrogenation catalyst selected from copper-containing and Group VIII metal-containing catalysts therein;
   (f) supplying to the at least one other hydrogenation zone, in a second phase of operation, a vaporous feed stream comprising a hydrogen-containing gas and the unsaturated organic compound;
   (g) maintaining the at least one other hydrogenation zone, in the second phase of operation, at a temperature in the range of from about 150° C. to about 350° C. and a pressure in the range of from about 150 psia up to about 2000 psia;
   (h) recovering from the at least one other hydrogenation zone, in the second phase of operation, a reaction product stream comprising the alcohol or diol; and
   (i) supplying to the at least one hydrogenation zone, in the second phase of operation, a stream of hydrogen-containing gas thereby to reactivate the charge of hydrogenation catalyst therein.

2. A process according to claim 1, in which the stream of hydrogen-containing gas of at least one of steps (e) to (i) comprises a hot stream of recycle and make-up gas.

3. A process according to claim 1, in which there is recovered from at least one of steps (e) and (i) a stream of hydrogen-containing gas which is admixed with a vaporous hydrogen-containing stream of the unsaturated organic compound to form the vaporous feed stream of the corresponding one of steps (b) and (f).

4. A process according to claim 1, in which there is recovered from at least one of steps (e) and (i) a stream of hydrogen-containing gas which is admixed with the reaction product stream of the corresponding one of steps (d) and (h).

5. A process according to claim 1, in which there is recovered from at least one of steps (e) and (i) a stream of hydrogen-containing gas which is used to vaporise the unsaturated organic compound and to form a vaporous hydrogen-containing stream of the unsaturated organic compound.

6. A process according to claim 1, in which the vaporous feed stream of at least one of steps (b) and (f) is formed by admixing hot recycle gas with a vaporous hydrogen-containing stream of the unsaturated organic compound.

7. A process according to claim 6, in which the vaporous hydrogen-containing stream of the unsaturated organic compound of steps (b) and (f) is substantially saturated with the unsaturated organic material.

8. A process according to claim 1, in which the vaporous feed stream of at least one of steps (b) and (f) is at a feed temperature at least about 5° C. above its dew point.

9. A process according to claim 1, in which the direction of flow of the stream of hydrogen-containing gas through the respective hydrogenation zone or zones in at least one of steps (e) and (i) is the same as the direction of flow of the vaporous feed stream through that zone in the corresponding one of steps (b) and (f).

10. A process according to claim 1, in which the direction of flow of the stream of hydrogen-containing gas through the respective hydrogenation zone or zones in at least one of steps (e) and (i) is the opposite to the direction of flow of the vaporous feed stream through that zone in the corresponding one of steps (b) and (f).

11. A process according to claim 1, in which the temperature and pressure maintained in paragraphs (c) and (g) comprise a temperature of from about 200° C. to about 260° C. and a pressure of from about 450 psia (about 31.03 bar) to about 1000 psia (about 68.95 bar).

12. A process according to claim 1, in which the unsaturated organic compound comprises dimethyl 1,4-cyclohexanedicarboxylate and in which the hydrogenated product comprises 1,4-cyclohexanedimethanol.

13. A process according to claim 1, in which the unsaturated organic compound comprises dimethyl 1,2-cyclohexanedicarboxylate and in which the hydrogenated product comprises 1,2-cyclohexanedimethanol.

14. A process according to claim 1, in which the unsaturated organic compound comprises dimethyl 1,3-cyclohexanedicarboxylate and in which the hydrogenated product comprises 1,3-cyclohexanedimethanol.

15. A process according to claim 1, in which the unsaturated organic compound comprises an ester selected from dimethyl and diethyl maleate and in which the hydrogenated product comprises butane-1,4-diol.

16. A process according to claim 1, in which the period used for reactivation ranges from about 1 hour up to about 24 hours.

17. A process according to claim 1, in which the reactivation temperature of step (e) lies in the range of from about 150° C. to about 350° C. and is from about 50° C. less than to about 50° C. more than the feed temperature of the vaporous feed stream to the hydrogenation zone.

18. A process according to claim 17, in which the copper-containing catalyst is selected from reduced copper chromite, reduced promoted copper chromite, and manganese promoted copper catalysts.

* * * * *